United States Patent [19]
Cox et al.

[11] Patent Number: 5,243,848
[45] Date of Patent: Sep. 14, 1993

[54] DETERMINING THE VOLUME OF GASES IN TRANSFORMER COOLING OIL

[75] Inventors: Brian M. Cox; Dudley R. Medhurst, both of Surrey, England

[73] Assignee: The National Grid Company PLC, London, England

[21] Appl. No.: 870,565

[22] Filed: Apr. 17, 1992

[30] Foreign Application Priority Data

Jun. 18, 1991 [GB] United Kingdom ............... 9113067

[51] Int. Cl.$^5$ ............................................. G01N 7/00
[52] U.S. Cl. .................................. 73/19.05; 73/19.11; 73/19.12
[58] Field of Search ................ 73/19.1, 19.01, 19.05, 73/19.02, 19.11, 19.12, 31.07, 23.41; 55/55, 189; 417/443, 444, 545, 552, 511

[56] References Cited

U.S. PATENT DOCUMENTS

| | | | |
|---|---|---|---|
| 3,844,160 | 10/1974 | Yamaoka | 73/19.11 |
| 4,236,404 | 12/1980 | Ketchum et al. | 73/19.11 |
| 4,409,814 | 10/1983 | Onuma et al. | 73/19.11 |
| 4,518,328 | 5/1985 | Nemoto | 417/511 |
| 4,763,514 | 8/1988 | Naito et al. | 73/19.11 |
| 4,764,344 | 8/1988 | Knab | 73/19.01 |
| 4,972,721 | 11/1990 | Conti | 73/37.5 |

Primary Examiner—Hezron E. Williams
Assistant Examiner—Michael Brock
Attorney, Agent, or Firm—McAulay Fisher Nissen Goldberg & Kiel

[57] ABSTRACT

Apparatus for determining the volume of gas dissolved or entrapped in transformer cooling oil includes an oil receiver, a metering space and a piston pump arranged to apply a reduced pressure to oil in the receiver and to transfer the gas which is liberated from the oil into the metering space. The piston pump is connected to and controlled by a controller. The metering space comprises a cylinder which accommodates a piston which is connected to be moved by an actuator which is connected to and controlled by the controller. The pressure detector is provided which is responsive to the pressure in the metering space and is arranged to deliver a signal indicative of the magnitude of the pressure to the controller. A transducer is connected to the controller and is arranged to produce a signal, when the said pressure reaches a predetermined value, which is indicative of the volume of gas within the metering space.

9 Claims, 4 Drawing Sheets

DETERMINING THE VOLUME OF GASES IN TRANSFORMER COOLING OIL

BACKGROUND OF THE INVENTION

1. Field of the Invention

The present invention relates to apparatus for determining the condition of a transformer and is concerned with apparatus for extracting and determining the volume and composition of gases dissolved or entrapped in transformer cooling oil.

2. Description of the Related Art

It is usual for relatively high power transformers, as are used in e.g. diesel electric locomotives and for stepping up or down the voltage in the high voltage electricity transmission grid, to include a volume of oil in cooling passages, through which the oil is generally pumped, in order to dissipate the heat generated by the transformer to the atmosphere. If such a transformer should develop a fault, such as a local short circuit, additional heat is generated at that point and this is transmitted to the oil in the vicinity of the fault. This additional heat results in thermal degradation of the oil and thus in the generation of gases which dissolve in the oil or remain entrapped in it in the form of small bubbles. The composition of these gases gives an indication of the temperature at the fault and thus of the nature of the fault and the volume of the gases provides an indication of the severity of the fault.

It is known to check the condition of a transformer by periodically removing a sample of the oil and determining the composition and volume of gas therein so as to detect the possible presence of a fault which can not be readily recognised by other means. For example, with reference to the apparatus of FIG. 1, this apparatus includes an oil receiver 2 which is connected to an oil inlet line 4 and to a dump tank 6 via an oil outlet line 8. The receiver 2 is also connected via a vacuum line 10 to a vacuum source 12, which is also connected to a pressure gauge 14, and via a gas outlet line 16 to a Toepler pump 18. A Toepler pump has only a single port and comprises a vessel containing mercury whose level within the vessel may be manually raised and lowered to expel or induce gas through the port. The port of the Toepler pump is connected via an outlet line 20 to a metering space or transparent burette 22 which contains visible volumetric markings and which also contains a volume of mercury which is in communication with further mercury in a mercury reservoir 24. The mercury within the burette 22 is also in communication with further mercury contained in an open-topped levelling vessel 26, whose function will be explained below. The top of the burette 22 also communicates via a line 28 with an analysing apparatus, typically a gas chromatograph 30. The various lines referred to above include a number of stopcocks or valves, whose purpose will be described below.

In use, the whole apparatus is evacuated by the vacuum pump 12 to a predetermined suitable vacuum by opening the valves 38,40,42,44,46,48 and 51. A sample of transformer cooling oil is tapped off into a sample bottle 32 and the oil inlet line 4 is introduced into the bottle and the valves 34 and 35 in the inlet line are opened briefly and then closed to flush the line 4. The valves 38 and 46 are closed and oil is drawn into the calibrated receiver 2 by opening valves 34 and 36 until it is visually determined to have reached a predetermined level. The valve 36 is then closed and the valve 48 is adjusted to connect the line 20 to the burette 22. The oil is stirred with a magnetically operated stirrer to aid removal of gas from the oil. The valves 44 and 46 are then closed and opened respectively and the mercury in the Toepler pump is raised to expel gas into the burette. The valves 44 and 46 are then opened and closed respectively and the mercury level in the Toepler pump is lowered to recreate a vacuum for further extraction of gas from the oil. This process is repeated a number of times until most of the gas in the oil has been transferred into the burette and the burette valve 48 is then closed. The height of the levelling vessel 26 is then adjusted manually until the levels of the mercury within it and the burette are the same which indicates that the gas within the burette is at atmospheric pressure. The volume of this gas is then read visually from the calibrations on the burette. The valve 51 is then closed and valve 48 opened to connect the burette 22 to the evacuated line 28 and the gas chromatograph 30. The height of the levelling vessel 26 is adjusted further to reassert atmospheric pressure within the line 28 and gas chromatograph 30. The gas chromatograph is then manually started to analyse the contained gas. The volume and composition of the gas within a known volume of transformer oil are thus determined and the condition of the transformer and an indication of the nature and severity of any fault in the transformer may be derived from these values.

Whilst the apparatus referred to above is adequate for its purpose, it suffers from two major disadvantages. Firstly, the operation of the Toepler pump, the determination of the gas volume and the operation of the numerous valves are all manual operations which means that the use of the apparatus is extremely laborious and time consuming and thus expensive. In practice, it is difficult for an operative to analyse more than about ten oil samples per day. Secondly, the apparatus includes a relatively large volume of mercury which represents a considerable potential hazard to the health of the operative and to the environment, particularly if breakage of any of the mercury-containing vessels should occur.

The object of the invention is therefore to provide apparatus for determining the volume and preferably also the composition of the gases in transformer oil which suffers from neither of the disadvantages referred to above.

SUMMARY OF THE INVENTION

According to the present invention, apparatus for determining the volume of gas dissolved or entrapped in transformer cooling oil of the type including an oil receiver, a metering space and a pump which is arranged to apply a reduced pressure to oil in the receiver and to transfer the gas which is liberated from the oil into the metering space is characterised in that the pump comprises a piston pump which is connected to and controlled by a controller, that the metering space comprises a cylinder which accommodates a piston which is connected to be moved by an actuator which is connected to and controlled by the controller, that a pressure detector is provided which is responsive to the pressure in the metering space and is arranged to deliver a signal indicative of the magnitude of the pressure to the controller and that means are provided which are connected to the controller and are arranged to produce a signal, when the said pressure reaches a predetermined value, which is indicative of the volume of gas within the metering space.

Thus in the apparatus in accordance with the invention the Toepler pump and the burette in the known apparatus are replaced by piston/cylinder units and the potential danger associated with the mercury which was previously used is eliminated. Furthermore, the pistons of the piston/cylinder units are moved under the control of a central controller, which may be in the form of a computer, so that the laborious and time-consuming steps of operating the Toepler pump and standardising the pressure in the burette prior to the volume measurement are conducted automatically under the control of the controller. This results in a considerable time saving. Due to the elimination of the balancing reservoir used in the known construction, it is necessary to devise some other means to standardise the pressure in the metering space at which its volume is determined. In accordance with the invention, this is achieved by a pressure detector, e.g. a transducer, which is subjected to the pressure in the metering space and is connected to the controller and indicates when the pressure has reached a predetermined value, which will usually be at least substantially atmospheric pressure. When the pressure in the metering space is at the predetermined value the volume of gas should be measured and this may be done by a variety of means. It would theoretically be possible for the cylinder of the metering space to be transparent and for the position of the piston to be determined visually but in the present invention the position of the piston is determined automatically and this information is fed to the controller and then displayed visually, either on a printout or on a screen. Many of the time-consuming steps which were necessary with the known apparatus are therefore eliminated and the apparatus of the present invention thus enables the volume of gas in the transformer oil to be determined very much more rapidly and accurately than was previously possible.

The piston pump which applies a reduced pressure to the oil in the receiver will include a piston which in practice only has two positions, i.e. fully extended and full retracted, and it is therefore convenient for it to be operated by a stepper motor controlled by the controller.

The means for producing a signal indicative of the volume of gas within the metering space may take a variety of forms and it is preferred that this acts indirectly, i.e. that means are provided which produce a signal indicative of the position of the associated piston rod. This can again be effected in a variety of ways, e.g. by optically determining the position of a positioning spot or movement of a series of such spots on the piston rod but it is preferred that a linear transducer is provided which is connected to the piston rod.

It is of course important that a known volume of oil is processed by the apparatus and in the known apparatus this was achieved visually, that is to say by checking that the correct volume of oil was present in the oil receiver. It is however preferred that the apparatus in accordance with the invention includes a balance or scales which receives a container containing oil to be introduced into the oil receiver and which is connected to the controller and arranged to supply to it a signal indicative of the weight of oil in the container. This container may thus be progressively filled until the balance indicates that it contains the correct weight of oil which is then transferred into the receiver or alternatively the balance may be used to indicate when the correct weight of oil has been withdrawn from the arbitrary amount within the container into the receiver.

It is preferred that the oil is withdrawn from the container into the receiver by means very similar to that used in the known apparatus and that the apparatus in accordance with the invention therefore includes an oil inlet pipe communicating with the oil receiver and means for applying a reduced pressure to the interior of the oil receiver and that there are two valves which are arranged in a respective one of these two pipes and which are connected to the controller and arranged to open or close on receipt of a signal from the controller. The application of the reduced pressure to the receiver and the induction of oil into it may thus be initiated and terminated automatically under the control of the controller.

Similarly, it is preferred that many or all of the valves which are necessarily provided, as in the known apparatus, are controlled by the controller, in particular the valves in the pipes which connect the oil receiver to the pump and the pump to the metering space.

The invention also embraces apparatus for determining the volume and composition of gas dissolved or entrapped in transformer cooling oil. Such apparatus will include apparatus of the type referred to above and means for analysing the gas, e.g. a gas chromatograph, connected to the metering space by a pipe which will necessarily include a valve. This valve is preferably also connected to the controller and arranged to open or close on receipt of a signal from the controller.

Further features and details of the invention will be apparent from the following description of one specific embodiment which is given by way of example with reference to FIGS. 2 to 5 of the accompanying drawings, in which:

DESCRIPTION OF THE PREFERRED EMBODIMENTS

Figure 1:
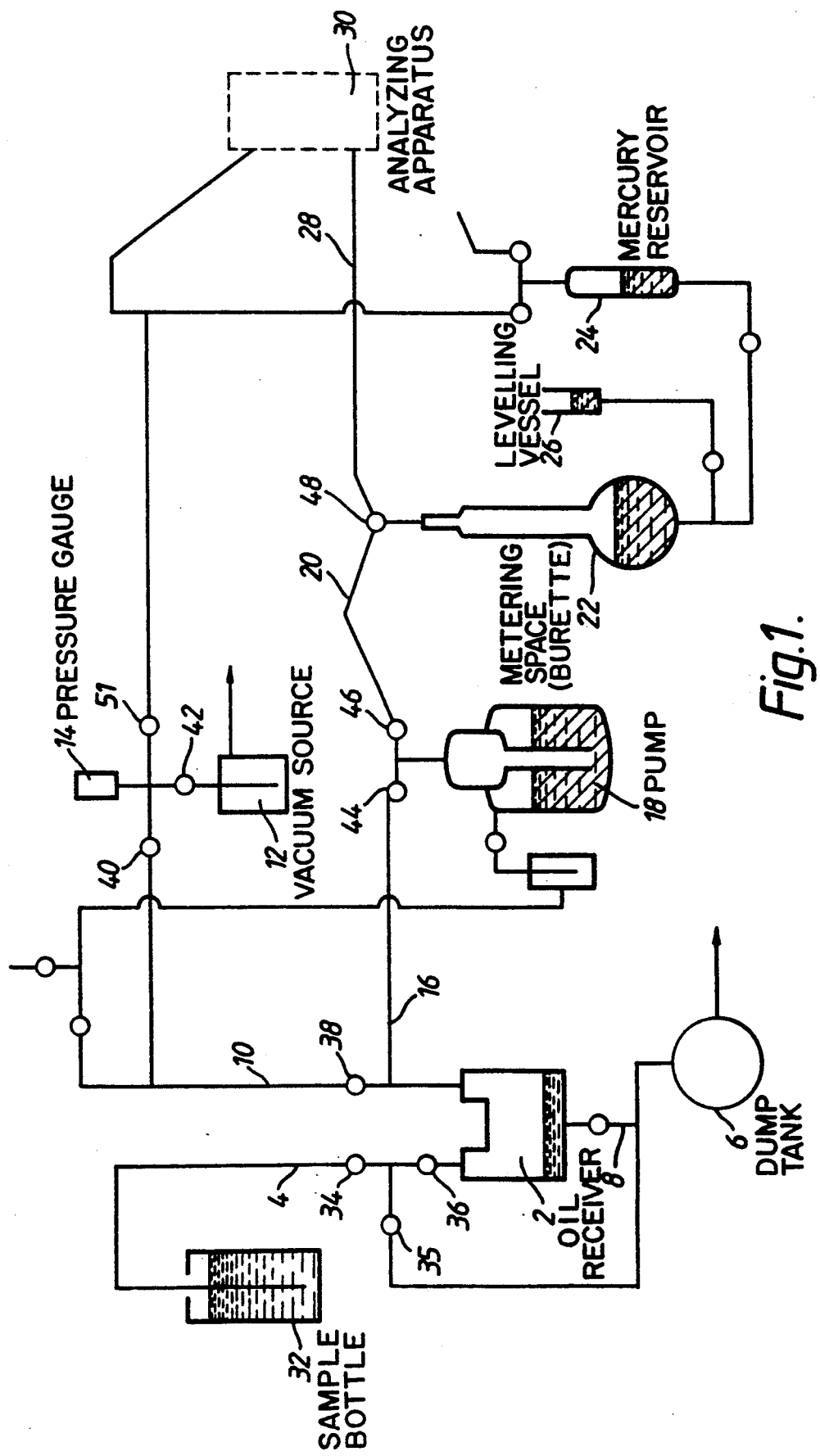
FIG. 1, previously described, is a schematic view of a known apparatus for extracting the gas from a sample of oil and determining its volume and composition.

Those components which are structurally or functionally the same as the corresponding component in the apparatus of FIG. 1 are designated with the same reference numeral.

As before, the apparatus includes an oil receiver 2, which is connected to a vacuum pump 12, a pump 18 and a metering space 22 which is connected to the outlet of the pump 18 and to the inlet of a gas chromatograph 30. However, the pump 18 is not of Toepler type but constitutes a piston pump comprising a cylinder 50 containing a piston 52 whose piston rod 54 is connected to a stepper motor 56. The metering space 22 also constitutes the cylinder of what may be regarded as a further piston pump. The piston 58 of this further pump is connected to a piston rod 60 which is in turn connected to a stepper motor 62 and to the actuating member 64 of a linear transducer 66. A pressure transducer 68 is connected to be subjected to the pressure within the cylinder 22.

The oil receiver 2 need no longer be transparent and the oil sample bottle 32 is received on an electrical or electronic balance 70 so that the amount of oil in the receiver is no longer determined visually but by reference to its weight in the sample bottle, from which it is transferred into the receiver.

Figure 2:
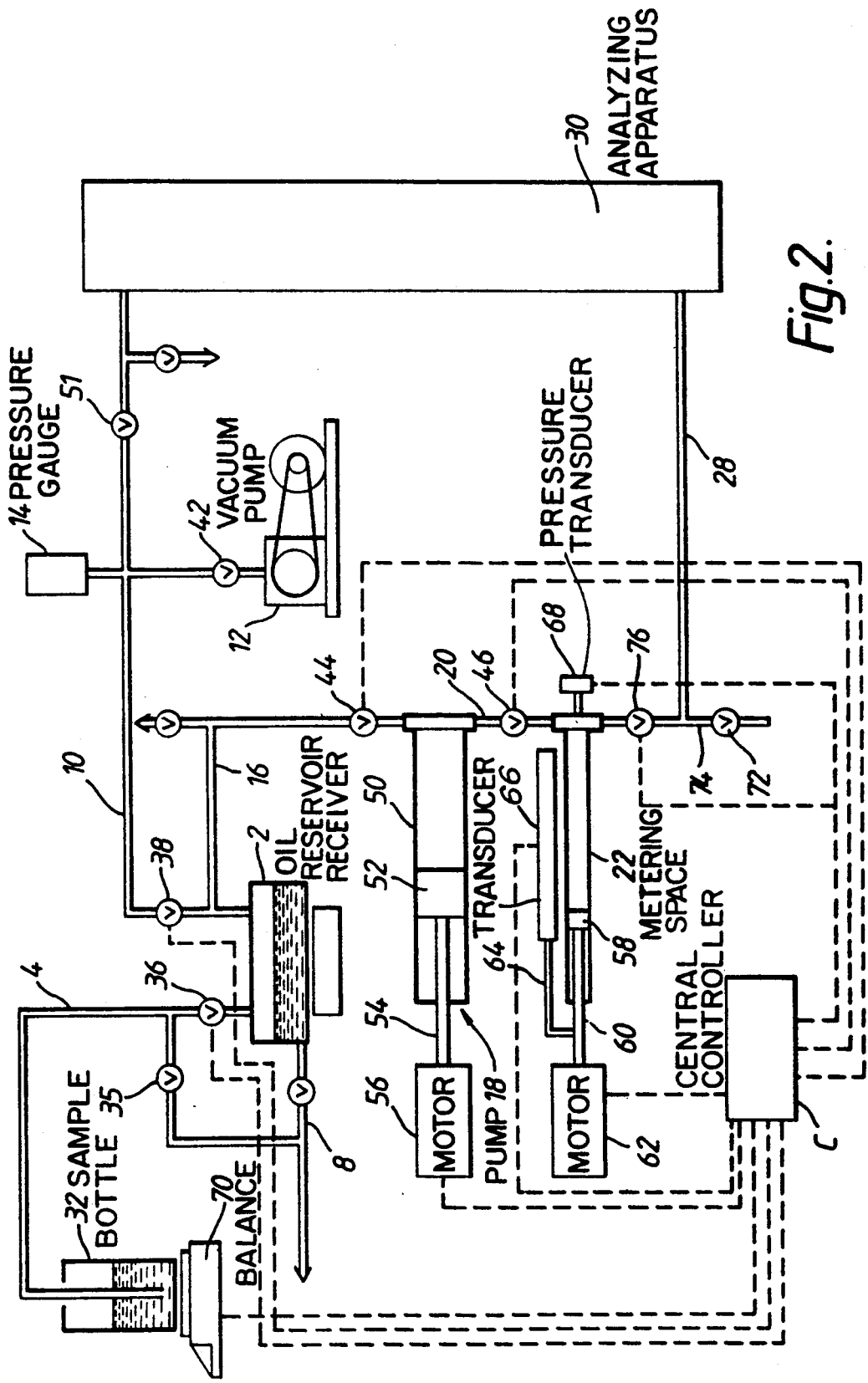
FIG. 2 is a diagrammatic view of a first embodiment of apparatus in accordance with the invention for determining the volume and composition of gas in a sample of transformer oil.

All the valves (which are shown in FIG. 2 by a circular shape) are pneumatically actuated. They, and also the motors 56 and 62 are connected to be controlled by a central controller C, e.g. a computer. The linear transducer 66 and pressure transducer 68 are also connected to deliver their output to the controller. Certain of the connections to the controller C are indicated in chain lines and the remainder have been omitted for the sake of clarity.

In use, the general sequence of operations as regards opening and closing of the valves and operation of the pump 18 is similar to that in the known construction. However, the opening and closing of the valves and the operation of the pump 18 are controlled automatically by the controller. When the pump is to apply a reduced pressure to the oil in the receiver, the motor 56 is actuated to retract the piston rod 54 and when the liberated gases are to be transferred to the metering space 22 the piston rod 54 is fully extended. When the pump 18 has performed a number of strokes predetermined by the controller, the valves 46 and 76 upstream and downstream of the metering space 22 are closed and the motor 62 is controlled to move until the transducer 68 indicates that the gas pressure in the space 22 is at a predetermined value, typically atmospheric pressure. The output of the linear transducer 66 at that time is indicative of the instantaneous position of the piston 58 and thus of the volume of gas released by the oil. The output of this transducer is supplied to the controller which produces a printed or other visual indication of the volume of gas in the metering space 22. The valve 76 is then opened and the gas in the space 22 is transferred into the pre-evacuated volume of the gas chromatograph 30, the gas pressure is re-established automatically to the predetermined value by extending the piston rod 60 under the control of the controller and pressure transducer 68. The gas chromatograph 30 is then started by a signal from the controller to analyse the gas in the usual way.

As explained above, the pump 18 applies a reduced pressure to the oil in the receiver 2 and this causes gas dissolved in the oil to be liberated. However, if there is a very substantial volume of gas dissolved in the oil, the rate at which it is liberated may cause foaming of the oil. If the foaming is particularly vigorous, oil may be transferred through the line 16 into the pump cylinder 50 and may degrade the performance of the pump 18 and the seals on the piston 52. This potential problem is eliminated by the modified construction which is illustrated in FIGS. 3 to 5.

Figure 3:
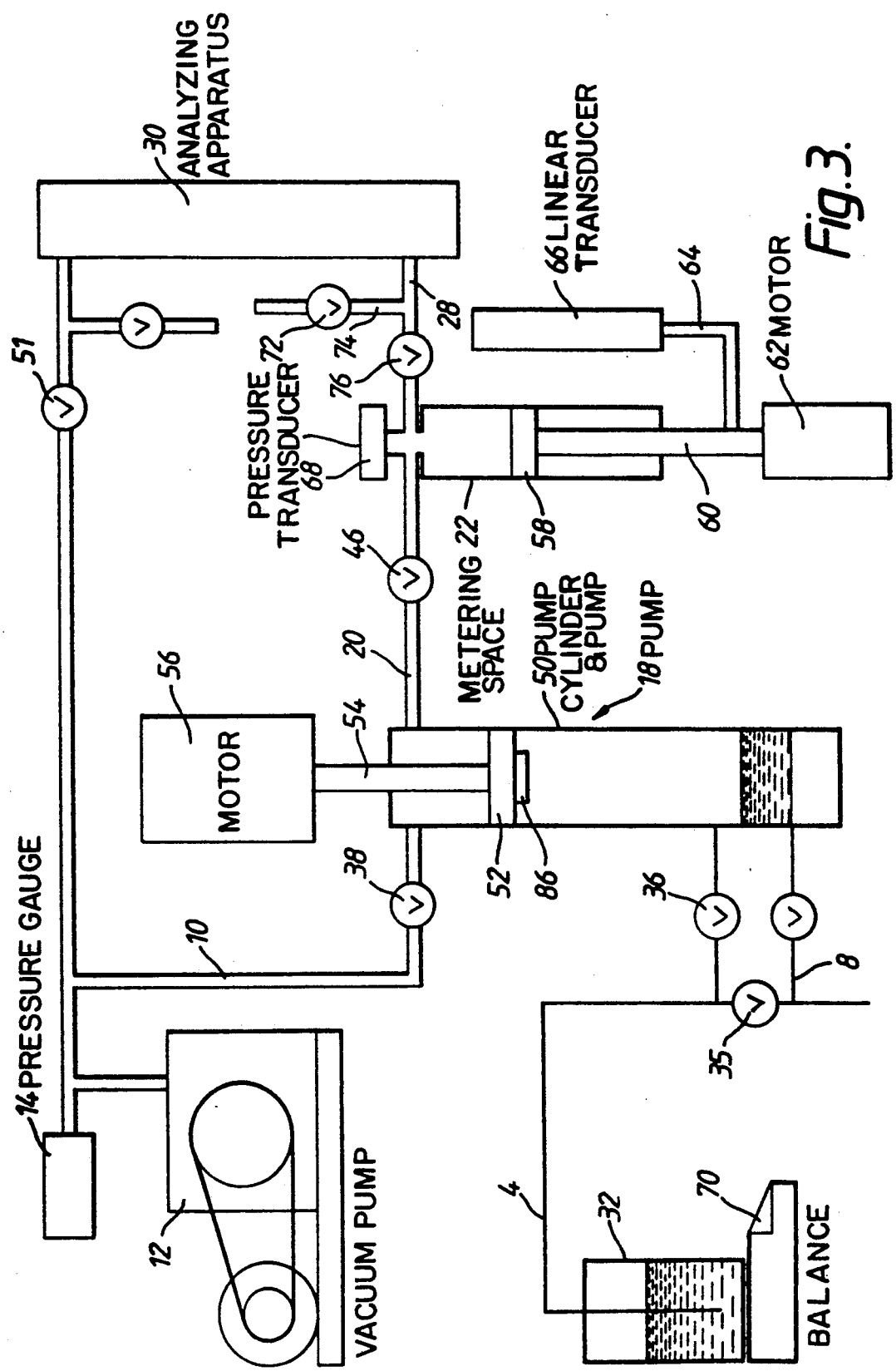
FIG. 3 is a view similar to FIG. 2 of a second embodiment in accordance with the invention from which the controller has been omitted for the sake of clarity.
Figure 4:
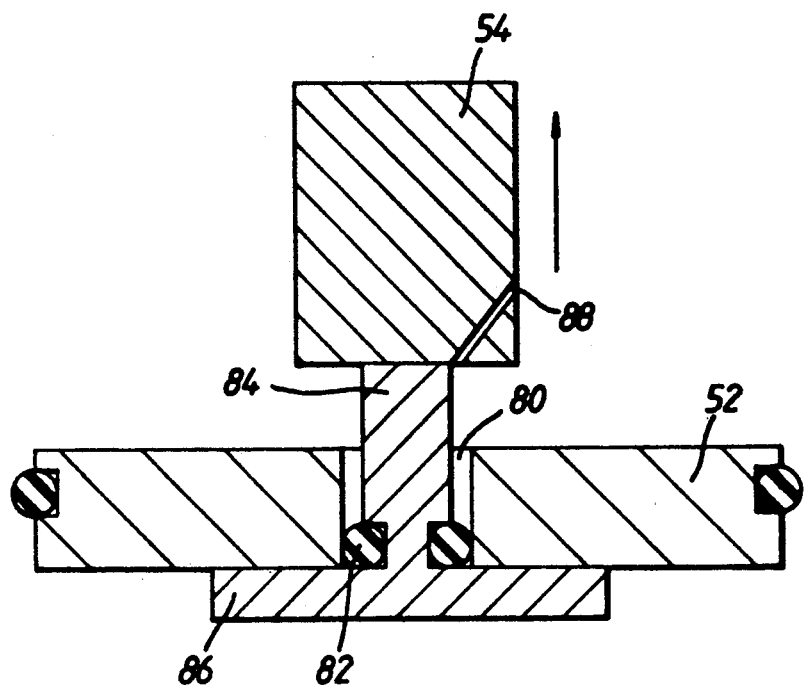
FIGS. 4 and 5 are scrap sectional views of the piston of the piston pump whilst performing its compression and transfer stroke, respectively.
Figure 5:
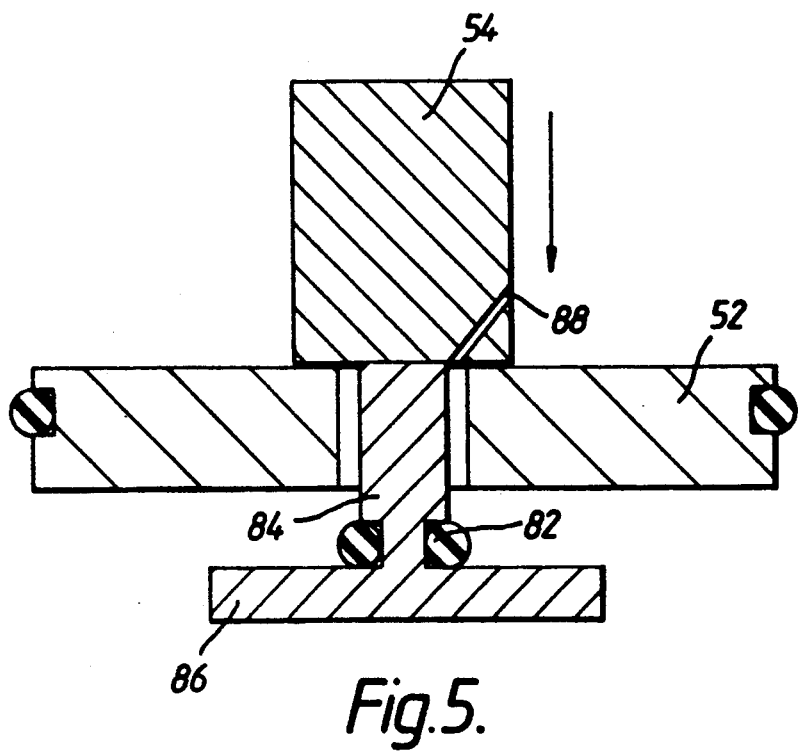

As may be seen from FIG. 3, the principal distinction of the second embodiment is that instead of the receiver and the pump being wholly separate, the receiver is constituted by the pump cylinder 50 and the piston 52 is provided with a one-way valve, which essentially replaces the valve 44 in the embodiment of FIG. 2 and which permits gas to pass through it when the piston is on its downstroke, as seen in FIG. 5, but not when it is on its upstroke. It will be appreciated that on its downstroke the piston transfers gas which has been liberated from the oil into the line 20 and this stroke may therefore be termed the transfer stroke. On its upstroke the piston subjects the oil to a reduced pressure and the gas in the line 20 to an increased pressure and this stroke may therefore be termed the compression/expansion stroke. The one-way valve may take various forms but in this embodiment, as seen in FIGS. 4 and 5, it is constituted by a clearance 80 between the piston 52 and the piston rod 54 which is selectively sealed by an O ring 82. At its end closest to the piston 52 the piston rod 54 has a portion 84 of reduced diameter at whose free end is a head 86. The portion 84 passes through an axial hole in the piston 52 and its diameter is less than that of the hole thereby defining the annular clearance 80. The length of the portion 84 is greater than the thickness of the piston 52. The piston rod 54, and thus also the portion 84 and the head 86, can therefore move axially to a limited extent with respect to the piston. An annular recess formed in the reduced diameter portion 84 adjacent the head 86 receives the O ring 82 which is arranged to form a seal with the surface of the hole in the piston.

When the piston 52 is on its upstroke and is thus applying a reduced pressure to the oil in the receiver or pump cylinder 50, the piston rod 54 and the piston 52 adopt the relative positions shown in FIG. 4 in which the head 86 engages the underside of the piston and the O ring 82 is received within the hole in the piston thereby preventing any communication between the two sides of the piston. When the piston is on its downstroke, the piston rod and piston adopt the relative positions shown in FIG. 5 in which the O ring 82 has moved out of the hole in the piston rod and the gas can flow through the piston from its underside to its upper side. At this time the shoulder on the piston rod at the junction of the full and reduced diameter portions engages the upper surface of the piston but it can be ensured that it does not form a seal with it and thus prevent the flow of gas. Alternatively or additionally, the full diameter portion of the piston rod 54 may have a vent passage 88 formed in it which communicates with the clearance 80 and with the side surface of the piston rod.

If foam should form on the surface of the oil whilst the piston performs its upstroke, the foam structure is largely destroyed when the piston performs its downstroke by virtue of the piston effectively crushing the foam and this fact coupled with the relatively narrow and tortuous path which the gas follows through the piston means that substantially no oil is carried to a position beyond the piston. In other respects the construction and operation of the second embodiment are substantially the same as those of the first embodiment.

Obviously, numerous modifications and variations of the present invention are possible in the light of the above teachings. It is therefore to be understood that within the scope of the appended claims, the invention may be practiced otherwise than as specifically described wherein.

What is claimed as new and desired to be secured by Letters Patent of the United States is:

1. Apparatus for determining the volume of gas dissolved or entrapped in transformer cooling oil, said apparatus including an oil receiver, a metering space, a controller and a pump which is arranged to apply reduced pressure to oil in said receiver to cause the gas dissolved or entrapped in said oil to be liberated and to transfer the gas which is liberated from said oil into said metering space, said pump comprising a cylinder which accommodates a piston connected to a piston rod, said cylinder further defining a housing for said oil receiver, said piston disposed for movement within said cylinder in a first direction toward said oil receiver which reduces the volume defined by the said cylinder and said piston and in a second direction opposite to said first direction and away from said oil receiver which increases the volume defined by said cylinder and said piston, movement of said piston in said first direction corresponding to its downstroke and movement of said piston on said second direction corresponding to its upstroke, said piston including a valve which is arranged to be open when said piston performs its downstroke and to be closed when said piston performs its upstroke, and said pump being connected to and controlled by said controller, said metering space comprising a cylinder which accommodates a piston, said piston being connected to be moved by an actuator, said actuator being connected to and controlled by said controller, a pressure detector being provided which is responsive to the pressure in said metering space and is arranged to deliver a signal indicative of the magnitude of said pressure to said controller, and means being provided which are connected to said controller and are arranged to produce a signal, when the said pressure reaches a predetermined value, which is indicative of the volume of gas within said metering space.

2. Apparatus as claimed in claim 1 wherein said pump includes a stepper motor controlled by said controller.

3. Apparatus as claimed in claim 1 wherein said means for producing a signal indicative of the volume of gas within said metering space comprises a linear transducer connected to move with said piston within said metering space.

4. Apparatus as claimed in claim 1 further including a balance which receives a container containing oil to be introduced into said oil receiver and which is connected to said controller and arranged to supply to said controller a signal indicative of the weight of said oil in said container.

5. Apparatus as claimed in claim 1 further including an oil inlet pipe communicating with said oil receiver, means for applying a reduced pressure to the interior of said oil receiver through a first pipe to draw oil into said receiver through said oil inlet pipe and first and second valves which are arranged in a respective one of the oil inlet pipe and the first pipe and which are connected to said controller and arranged to open or close on receipt of a signal from said controller.

6. Apparatus as claimed in claim 5 including a second pipe connecting said pump to said metering space and a third valve arranged in said second pipe, said third valve being connected to said controller and arranged to open or close on receipt of a signal from said controller.

7. Apparatus as claimed in claim 1 wherein said piston rod includes a portion of reduced cross sectional area which passes through a hole in said piston leaving a clearance and carries a sealing ring, said piston rod being capable of limited axial movement with respect to said piston whereby when said piston performs its downstroke the spaces on the two sides of said piston communicate through said clearance and when said piston performs its upstroke said clearance is sealed by sealing ring.

8. Apparatus for determining the volume and composition of gas dissolved or entrapped in transformer cooling oil, said apparatus including apparatus as claimed in claim 1 and means for analysing said gas connected to said metering space by a pipe including a valve.

9. Apparatus as claimed in claim 8 wherein said valve is connected to said controller and arranged to open of close on receipt of a signal from said controller.

* * * * *